(12) United States Patent
Schalk et al.

(10) Patent No.: US 8,532,756 B2
(45) Date of Patent: Sep. 10, 2013

(54) METHOD FOR ANALYZING FUNCTION OF THE BRAIN AND OTHER COMPLEX SYSTEMS

(75) Inventors: Gerwin Schalk, Glenmont, NY (US);
Eric Leuthardt, St. Louis, MO (US);
Jonathan Wolpaw, Delmar, NY (US);
Peter Brunner, Albany, NY (US)

(73) Assignee: Washington University, St. Louis, MO (US)

(*) Notice: Subject to any disclaimer, the term of this patent is extended or adjusted under 35 U.S.C. 154(b) by 848 days.

(21) Appl. No.: 12/304,953

(22) PCT Filed: Jun. 13, 2007

(86) PCT No.: PCT/US2007/071110
§ 371 (c)(1),
(2), (4) Date: Dec. 14, 2009

(87) PCT Pub. No.: WO2008/008589
PCT Pub. Date: Jan. 17, 2008

(65) Prior Publication Data
US 2010/0094154 A1   Apr. 15, 2010

Related U.S. Application Data

(60) Provisional application No. 60/813,062, filed on Jun. 13, 2006.

(51) Int. Cl.
*A61B 5/04* (2006.01)

(52) U.S. Cl.
USPC .......................................... 600/544; 600/545

(58) Field of Classification Search
USPC ................................................ 600/544–545
See application file for complete search history.

(56) References Cited

U.S. PATENT DOCUMENTS

| | | | |
|---|---|---|---|
| 5,406,956 A | 4/1995 | Farwell | |
| 6,304,775 B1* | 10/2001 | Iasemidis et al. | 600/544 |
| 2003/0088320 A1* | 5/2003 | Sale | 700/30 |
| 2004/0120557 A1* | 6/2004 | Sabol et al. | 382/128 |
| 2004/0133119 A1* | 7/2004 | Osorio et al. | 600/544 |
| 2005/0131311 A1 | 6/2005 | Leuthardt et al. | |

OTHER PUBLICATIONS

Gerwin Schalk, Eric C. Leuthardt, Peter Brunner, Jeffrey G. Ojemann, Lester A. Gerhardt, Jonathan R. Wolpaw, Real-time detection of event-related brain activity, NeuroImage, vol. 43, Issue 2, Nov. 1, 2008, pp. 245-249, ISSN 1053-8119, 10.1016/j.neuroimage.2008.07.037. (http://www.sciencedirect.com/science/article/pii/S1053811908008525).*

(Continued)

*Primary Examiner* — Michael Kahelin
*Assistant Examiner* — Karen Toth
(74) *Attorney, Agent, or Firm* — Armstrong Teasdale LLP (57) ABSTRACT

A method and system are provided for analyzing electromagnetic brain signals such as EEG and ECoG signals in a subject in real time and which avoids the need for time-intensive retrospective analysis of brain activity in the subject. This can be applied to all complex systems with multiple fluctuating signals to identify and predict significant events.

16 Claims, 8 Drawing Sheets

(56) References Cited

OTHER PUBLICATIONS

G. Schalk, P. Brunner, L.A. Gerhardt, H. Bischof, J.R. Wolpaw, Brain—computer interfaces (BCIs): Detection instead of classification, Journal of Neuroscience Methods, vol. 167, Issue 1, Jan. 15, 2008, pp. 51-62, ISSN 0165-0270, 10.1016/j.jneumeth.2007.08.010. (http://www.sciencedirect.com/science/article/pii/S0165027007004116).*

Branco et al, Functional variability of the human cortical motor map: electrical stimulation findings in perirolandic epilepsy surgery. J Clin Neurophysiol, 2003, 20:17-25.

Keles et al, Intraoperative subcortical stimulation mapping for hemispheric perirolandic gliomas located within or adjacent to the descending motor pathways: evaluation of morbidity and assessment of functional outcome in 294 patients, J Neurosurg, 2004, 100:369-375.

International Search Report in the related application PCT/US07/71110 issued on Jul. 7, 2008.

* cited by examiner

METHOD FOR ANALYZING FUNCTION OF THE BRAIN AND OTHER COMPLEX SYSTEMS

STATEMENT REGARDING FEDERALLY SPONSORED RESEARCH OR DEVELOPMENT

This invention was made in part with Government support under National Institutes of Health Grants HD30146 and EB00856. The Government has certain rights in the invention.

CROSS-REFERENCE TO RELATED APPLICATIONS

The following identified patent applications are relied upon and incorporated by reference in this application:

U.S. Provisional Patent Application No. 60/813,062, entitled "METHOD FOR ANALYZING FUNCTION OF THE BRAIN AND OTHER COMPLEX SYSTEMS", filed on Jun. 13, 2006.

International PCT Patent Application No. PCT/US2007/071110, entitled, "METHOD FOR ANALYZING FUNCTION OF THE BRAIN AND OTHER COMPLEX SYSTEMS", filed on Jun. 13, 2007.

INCORPORATION-BY-REFERENCE OF MATERIAL SUBMITTED ON A COMPACT DISC

Not Applicable.

FIELD OF THE INVENTION

The present invention generally relates to detection of signal changes in complex systems.

BACKGROUND

Many fields, such as clinical neurology, neurosurgery, and neuropsychology, as well as basic neuroscience research, require methods for detecting, localizing, characterizing, and (in some situations) predicting, normal and abnormal brain function. Since the late nineteenth century, invasive and non-invasive recordings of the electromagnetic (EM) activity resulting from brain function have been used for these purposes.

Brain function produces electrical and magnetic (EM) activity that can be recorded from the scalp (electroencephalographic activity (EEG)), from the surface of the brain (electrocorticographic activity (ECoG)), or from within the brain. This activity can be expressed in various ways, such as, for example, oscillations at different frequencies, voltage levels, or firing frequencies of individual cortical neurons. For many decades, these measures of brain function have been used clinically (e.g., to localize mass lesions such as tumors, to recognize seizures, to assess auditory, visual, and somatosensory pathways) (see generally Karbowski, Eur Neurol 30:170-175, 1990). They have also been used experimentally in both humans and animals to explore the anatomical and physiological bases of normal and abnormal brain function. At present, EM methods continue to be a mainstay of both clinical assessments and research explorations of brain function.

Yet, current approaches to studying brain function with any sensor modality (e.g., functional magnetic resonance imaging (fMRI), electroencephalography (EEG), magnetoencephalography (MEG), electrocorticography (ECoG), or single neuron recordings) are constrained by the fact that they are typically retrospective. This is because the brain signal change that is associated with a specific function or event is either unknown a priori or does not sufficiently generalize to a different individual to permit prospective (i.e., real-time) extraction of that signal with the requisite fidelity. Also, enormous inter- and intra-individual variations exist in the anatomical and physiological features of brain functions and in the EM activity that is associated with these functions. These serious limitations have prohibited prospective study of many important problems.

The requirement for extensive data collection under defined conditions and subsequent detailed analyses makes it difficult or impossible to use EM methods for a wide variety of important clinical and research purposes. As a result, only the grossest most obvious features of EM activity can be confidently used to assess, in a predefined standard way, brain function in individuals (e.g., the total absence of EEG for a defined period indicates brain death). In contrast, other clinical and experimental uses of EM activity typically require laborious collection of often extensive EM data under defined conditions from each individual, and subsequent elaborate analysis of these data to determine for that individual the relationships between specific aspects of brain function and specific features of EM activity.

Thus, for example, using EEG or ECoG to predict seizures in a person with epilepsy has only been possible after extensive study had defined for that person the exact differences (e.g., in frequency spectra) between the EEG or ECoG activity that preceded a seizure and the activity at other times.

As another example, using EEG to monitor state of alertness in a specific person is only possible after extensive study has defined the precise relationships between specific EEG features and specific states of alertness for that person.

The identification of cortical areas critical for specific functions such as speech is an essential prerequisite in surgery to remove epileptic foci, tumors, or vascular malformations. This identification currently requires difficult, repeated, and often traumatic electrical stimulation (ECS) of cortex (see e.g., Branco et al., J Clin Neurophysiol 20:17-25, 2003; Keles, J Neurosurg 100:369-375, 2004). ECS is coarse in its ability to delineate regions of motor and speech cortex and carries risks of inducing seizures or misidentifying critical areas. The capacity to passively locate spatially localized changes produced by movements and language would be a valuable neurosurgical tool that could augment or even replace current methods to locate function, such as ECS. However, these functional changes often manifest themselves in signal features that differ markedly from individual to individual, which prohibits the real-time detection of these changes by current methods. A passive method for identifying the cortical areas critical for specific functions, such as speech, could reduce the need for ECS and improve accuracy, but only if it did not entail prolonged data collection and subsequent analysis.

As described above, the requirement for extensive data collection under defined conditions and subsequent detailed analyses makes it difficult or impossible to use EM methods for a wide variety of important clinical and research purposes.

These same constraints exist for any complex system by which multiple signals are generated. Money markets, stock markets, astronomical phenomena, weather, or complex communication systems (e.g., level of chatter on the Internet) all require the same level of extensive retrospective analyses, thereby often eliminating the possibility of detecting or predicting significant events in a prospective fashion. A need exists for methods for detecting and analyzing signals of true events in such systems in real time.

SUMMARY OF THE INVENTION

Methods and systems consistent with the present invention are generally directed to detecting signal changes in complex systems, especially those systems with substantial inter- and intra-data set variability. Further, detailed a-priori knowledge of those changes is not required according to the methods and systems described herein. Among the various aspects consistent with the present invention is analysis of brain signal changes in a prospective real-time manner without extensive prior data collection and analysis, with readily interpreted results.

Briefly, therefore, methods and systems consistent with the present invention are directed to detecting changes in complex signals by establishing a comprehensive baseline and subsequently searching for statistical deviations from this baseline. This approach can be used with virtually any complex signal to detect a change in state. By creating and using a statistical model for the likelihood of the fluctuation for each feature evaluated for a given baseline condition, even subtle changes can be detected. The techniques described herein can eliminate or minimize the need for extensive data collection and retrospective analysis. These techniques allow one to create a model for event prediction without a priori assumptions or the benefit of extensive retrospective analyses.

The present teachings include a method for analyzing complex signals comprising obtaining a first signal having a plurality of signal features from a complex system during a null condition, and calculating a statistical distribution description for each signal feature of the first signal to establish a signal features baseline. In an exemplary embodiment of the method, a second signal is obtained from the complex system during a non-null condition and the signal features baseline is compared with each signal feature of the second signal to detect an event in the complex system. In an exemplary embodiment, the method occurs in real-time. The signals are, for example, electromagnetic (EM) signals from a physiological system, such as EM signals of brain activity in a subject, including, for example, electroencephalographic (EEG) signals, electrocorticographic (ECoG) signals, functional magnetic resonance (fMRI) signals, optical imaging signals such as near infrared (fNIR) signals, positron emission tomography (PET) signals of brain activity, or Single Photon Emission-Computed Tomography (SPECT) signals. In an exemplary embodiment, the non-null condition comprises the subject performing a task, such as a motor task or a language task, or the subject receiving a stimulus, or the subject telling the truth, or the subject telling a lie. The non-null condition may also comprise a change in the subject's level of alertness. The event is, for example, an event of abnormal brain activity such as seizure activity, or brain activity associated with a condition selected from the group consisting of stroke, demyelinating diseases, brain trauma, tumor, metabolic injury, epilepsy, meningitis, encephalitis, lead exposure, and developmental brain abnormalities. The event is alternatively an event of normal brain activity such as changes in brain activity associated with the non-null condition of the subject. The method can also be employed to characterize localized changes in brain activity by selecting a subset of signal features associated with localized brain activity; and comparing the selected subset of signal features in the signal features baseline with the selected subset of signal features in the second signal to characterize localized changes in brain activity.

In alternative embodiments, the EM signals from a physiological system comprise electrocardiographic (ECG) signals, or EM signals from non-cardiac organs such as muscle, lungs or intestines. In other alternative embodiments, the complex system signals comprise non-electromagnetic signals, which may arise from a physiological system, such as signals indicating sleep apnea, cardiopulmonary dynamics, blood pressure, blood oxygenation, and tremor, or from a non-biological complex system such as signals comprising financial market indices, stock market indices, environmental indices, weather indices, indices of complex machinery function and complex manufacturing indices, astronomical observation indices, indices of Internet communications, and indices of population dynamics, such as indices of infection.

In another aspect consistent with the present invention, a system is provided for analyzing brain signals comprising a plurality of brain electrodes for obtaining electromagnetic (EM) signals coupled to conducting material for conducting the EM signals from the plurality of brain electrodes, and a computer workstation configured to gather, store and display the EM signals from the plurality of brain electrodes. The computer workstation is configured to collect a first EM brain signal from a subject under a null condition, calculate a statistical distribution description for each signal feature of the first brain signal to establish a signal features baseline, collect a second brain signal from the subject during a non-null condition, and compare the signal features baseline with the signal features of the second brain signal to detect a brain event. The plurality of brain electrodes are, for example, electroencephalographic (EEG) recording electrodes, or electrocorticographic (ECoG) recording electrodes. The computer workstation is configured, for example, to analyze the brain signals in real time.

In another aspect consistent with the present invention, a system is provided for analyzing complex signals, comprising a computer workstation configured to electronically gather, store and display electronic signals from a complex system, the computer workstation configured to collect a first signal from the complex system under a null condition, calculate a statistical distribution description for each signal feature of the first signal to establish a signal features baseline, collect a second signal from the complex system during a non-null condition, and compare the signal features baseline with the signal features of the second brain signal to detect a brain event. In an exemplary embodiment the computer workstation is configured to analyze the brain signals in real time.

In another aspect consistent with the present invention, a method for analyzing complex signals in a system is provided, the method comprising, for each of a plurality of time points t of a first signal from the system under a null condition, using the vector of frequency domain amplitudes to generate a first set of Gaussian distributions Y describing the statistical distribution of the brain signal, wherein each Gaussian distribution j has a mean feature vector $\mu_j$, a covariance matrix $\Sigma_j$ and a prior probability $w_j$, wherein the number of Gaussian distributions Y is determined by iteratively choosing Y to minimize the Akaike Information Criterion, and for a second signal of the system obtained under a non-null condition, repeating the step of generating a set of Gaussian distributions Y to obtain a second set of Y Gaussian distributions. In an exemplary embodiment, the method further comprises determining the fit of the second set of Y Gaussian distributions to the first set of Y Gaussian to determine the probability that the second signal under the non-null condition varied from the first signal under the null condition by chance alone.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

As used herein, the term "brain signal" refers broadly to any signal reflecting the electromagnetic (EM) or metabolic activity of a brain, including without limitation electroencephalographic activity (EEG), and electrocorticographic (ECoG) activity or activity detected though functional magnetic resonance imaging (fMRI), magnetoenecpalography, optical imaging, positron emission tomography, or Single Photon Emission-Computed Tomography, or near-infrared (fNIR) imaging.

As used herein, the term "signal features" refers broadly to identifiable characteristics of any complex signal, including such characteristics as frequencies and amplitudes, voltage levels, low frequency oscillations. For certain types of biological signals such as electromagnetic signals and signals of metabolic activity in the brain, signal features also include characteristics such as nerve cell firing rates and indices of altered metabolism such as change in blood flow, oxygen absorption, or glucose metabolism.

As used herein, the term "null condition" refers broadly to the state of a complex system in which the system is determined to be at a starting reference or baseline state. A non-limiting example is a human subject not performing an overt or imagined task and not receiving an identified stimulus and not in the midst of a specific event (such as an epileptic seizure), but instead at rest in terms of performing a task or receiving stimuli, or in a normal state (e.g., no seizure).

As used herein, the term "non-null condition" refers to the state of a complex system in which the system is perturbed from the baseline state and is no longer at the baseline state or null condition, such as a human subject who has been asked to perform or is in the process of performing a task or is receiving some form of stimuli, or is experiencing an abnormal event (e.g. seizure).

As used herein, the term "signal features baseline" refers to a set of Gaussian distributions that describes a plurality of signal features of a complex signal obtained during the null condition.

As used herein, the term "event" refers broadly to an occurrence of a change of activity in a complex system.

As used herein the term "brain event" refers broadly to the occurrence of abnormal activity in the brain such as activity associated with a seizure, or the occurrence of normal functional activity such as a functionally significant change in brain activity associated with the performance of a task or reception of stimuli.

As used herein, the term "task" refers broadly to a mental or physical activity performed by a subject possibly in response to a specific instruction or stimulus, for the purpose of providing a non-null condition. A task includes, for example, simple motor tasks such as small hand or arm movements or protruding the tongue or speaking a word, and also simple cognitive tasks such as imagining but not actually executing an action of the feet or hands. The term "stimulus" refers broadly to any form of activity or agent applied to the subject that can be detected by any of the sensory organs. A stimulus example includes for example, visual images that are presented by a computer screen, sounds that are emitted by speakers, smells that are emitted in the subject's presence, specific textures applied to the subject's skin, or flavors given to the subject to eat or drink.

As used herein, the term "real-time" refers not only to the speed of computation, but also to the capacity of methods and systems consistent with the present invention to perform these signal detections in ongoing signals (i.e., in a prospective rather than retrospective fashion). The speed is sufficient to accurately provide to an observer (e.g., a scientist or physician) an indicator of system events as they are actually occurring.

Methods and systems consistent with the present invention are generally directed to detecting signal changes in systems with substantial inter- and intra-data set variability without detailed a-priori knowledge of those changes. In several embodiments, the signal changes are brain signal changes. This approach facilitates the detection, localization, characterization, and even prediction of signal changes in complex systems in a prospective real-time manner without extensive prior data collection and analysis, with readily interpreted results.

Briefly, signal charges are detected according to a process termed SIGnal modeling For Real-time Identification and Event Detection, or "SIGFRIED", which establishes a comprehensive baseline for a signal and subsequently detects statistical deviations from this baseline. For example, the technique allows one to detect and localize brain function in real time by quickly establishing for each individual the baseline characteristics of a comprehensive set of EM (or other) features (e.g., a wide range of frequency bands, voltage levels, or neuronal firing rates) and then in a prospective fashion look for deviations from these baseline characteristics. By creating and using a statistical model for the likelihood of the fluctuation for each feature evaluated for a given baseline condition, even subtle changes can be detected. This strategy can eliminate the need for extensive data collection and retrospective analysis, greatly extending the usefulness of various clinical and research protocols.

The SIGFRIED algorithm creates statistical models of fluctuating signals and supports sensitive detection and prediction of alterations in state of a complex system. It can be used with any complex signal to detect a change in state. As such, SIGFRIED is useful for, for example, analyzing EM signals of physiological phenomena such as cardiac rhythms/ EKG, EM signatures from other organs (e.g., muscles, lungs, intestines), and also non-EM physiological signals (e.g., measures of cardiopulmonary dynamics, blood pressure, blood oxygenation, tremor, etc.). Thus, SIGFRIED could be used conveniently and without laborious preparation for a variety of tasks such as to localize cortical function during surgery, to predict (and thus perhaps abort) seizures, to detect changes in alertness (and thus prevent errors), etc. SIGFRIED can also have applications to other non-biological fluctuating systems such as, for example, money markets, stock markets, environmental weather indices, function of complex machinery, complex industrial systems (e.g. multi-step chemical and manufacturing processes), rhythmic astronomical phenomena (e.g., solar flares), and chatter associated with security monitoring, and population monitoring for disease outbreaks.

Furthermore, this technique allows one to create a model for event prediction without a priori assumptions or the benefit of extensive retrospective analyses. Thus, for diseases such as epilepsy, subtle changes in the brain that precede a seizure could be detected as deviations from baseline, and their detection could potentially allow intervention that aborts the seizure. The technique is not limited to detecting changes in brain activity associated with epilepsy or seizure activity per se, but is also applicable to detecting changes in brain activity associated with pre-seizure states, stroke, demyelinating diseases, brain trauma, tumor, metabolic injury, epilepsy, meningitis, encephalitis, lead exposure, and developmental brain abnormalities.

Conventional approaches to detailed clinical or experimental analysis of brain function are typically retrospective. This is because the complexity of brain signals either does not permit direct interpretation of the real-time signals acquired directly from a sensor or because such interpretation requires a highly trained expert. To convert these complex signals into results that can be readily understood, conventional methods apply statistical methods after all data are collected. Because these retrospectively determined statistical relationships vary greatly within and between individuals, the real-time detection, localization, or prediction of brain function is difficult or impossible.

Described herein therefore is a new method for real-time analysis of complex systems that is readily interpreted by a non-expert or by an algorithm. SIGFRIED can, for example, visualize brain signal changes in a prospective real-time manner without extensive prior data collection and analysis, and the results can be readily interpreted. This tool for real-time visualization of brain function can open up many new avenues for the study of normal and abnormal brain function. For example, when paired with ECoG, SIGFRIED can produce results that can be readily interpreted by an untrained observer without averaging and could reduce or eliminate the need for direct cortical stimulation. ECoG is an invasive procedure, requiring a craniotomy for electrode placement, and provides a combination of high spatial resolution on the order of 1-2 mm with a broad frequency range of approximately 0-200 Hz.

As another example, SIGFRIED can be paired with EEG. EEG is non-invasive procedure that provides spatial discrimination of approximately 3 centimeters and an appreciable frequency range of 0-40 Hz. When paired with EEG, SIGFRIED can, for example, identify the brain signals suited for brain-computer interface (BCD-based communication and control without elaborate retrospective analyses and prolonged testing of alternative signal features (see, US App. Pub. No. 2005-0131311, incorporated herein by reference). As a further example, SIGFRIED can be paired with Magnetoencephalography (MEG). MEG is a non-invasive modality with a similar profile to that of EEG. It has a spatial resolution of approximately 4 to 10 millimeters.

Briefly, SIGFRIED implements the concept that features of a signal input (e.g., the signal amplitudes at different frequencies, ranges of frequency bands, voltage levels, neuronal firing rates) during a null condition (e.g., EM brain signals of a non-performing or non-stimulated subject) can be comprehensively characterized by establishing a statistical description of that signal activity. Examples of cortical events linked to signal features include, but are not limited to, time-locked neuronal changes induced by sensory stimuli known as event related potentials (ERPs), or ongoing non-phase-locked fluctuations associated with frequency power changes, or changes in local motor potential (LMP), or alterations in firing rate of neurons, or alterations in metabolism such as changes in glucose metabolism, oxygen uptake, or blood flow, and the like. ERPs reflect transient synaptic and neuronal responses triggered by a specific stimulus. The frequency power changes are likely due to increases or decreases in the synchrony of the intrinsic oscillations of the underlying neuronal populations. Changes in metabolism are likely phenomena related to the increased or decreased energy requirements of synaptic and neuronal populations engaged in a given task. In contrast to techniques that derive one mean signal baseline value for each individual signal feature, SIGFRIED can capture the statistical distribution of each individual signal feature and its interactions with all other features.

SIGFRIED uses a mixture of Y Gaussian distributions where the number of Gaussians Y is automatically determined so as to most effectively describe the original signal distribution. Using this description, SIGFRIED subsequently compares, in real time and for each signal input, the current set of all signal features to the null state condition signal description and calculates from all features the probability (i.e., one single number for each location or a set of locations) that the currently observed signal was produced by the null state condition signal distribution. Significant changes can be readily visualized on a display. Working examples of this technique demonstrate real-time or near real-time visualization and localization of changes that occur in ECoG or EEG activity during motor or language function (see, e.g., Example 1 and Example 2 below). Signal acquisition, feature extraction, SIGFRIED processing, and visualization of change may occur with no more than, for example, a 100-msec lag.

A more detailed explanation of the SIGFRIED process is as follows. For each time point t in the resting data set, the vector of features (e.g., frequency domain amplitudes determined from the brain or any other complex system) $X_t=[X_{1,t}, \ldots, X_{D,t}]$ is input to a Competitive EM (CEM) algorithm (Celeux and Govaert, 1992, which is incorporated herein by reference) that has been modified and extended as described below. This procedure produces a model consisting of Y Gaussian distributions that approximate the statistical distribution of the features in the resting data set. Each of these Gaussian distributions j is characterized by a mean feature vector $\mu_j$, a covariance matrix $\Sigma_j$, and a prior probability $w_j$.

The fit of the Gaussian mixture model to the original distribution is assessed using the maximized negative log likelihood $L_j$ calculated for all Y Gaussian distributions j in the resting data distribution $$\left( L_j = \sum_{t=1}^{N_j} -\log\left(\frac{w_j}{(2\pi)^{\frac{D}{2}}|\Sigma_f|^{\frac{1}{2}}} e^{-\frac{m(X_t|j)}{2}}\right), \right.$$

$$\left. m(X_t \mid j) = (X_t - \mu_j)^T \Sigma_j^{-1} (X_t - \mu_j) \right).$$

Furthermore, the number of distributions Y is automatically determined by iteratively choosing Y such that it minimizes the Akaike Information Criterion $$\left( AIK(Y) = -2 \sum_{j=1}^{Y} L_j + 2N_p, \right.$$

with $N_p$ equal to the number of parameters in the model (Akaike, 1973)).

When applied to a new data point, the output of SIGFRIED is the negative log likelihood L calculated for that single point. It will be apparent that other algorithms can be used to calculate from all signal features the probability that a currently observed signal was produced by the null state condition signal distribution. Such algorithms include, for example, radial basis functions, kNN algorithms, Parzen windows, and the like.

SIGFRIED can also be used, for example, to detect and localize prospectively the cortical neurons associated with specific brain functions; to anticipate changes in alertness; to predict subsequent actions (e.g., movements) or events (e.g., seizures; see, Example 3, FIG. 4); to detect higher level differences in brain function (e.g., telling the truth versus lying); and for other purposes. Furthermore, by applying SIGFRIED to a given set of brain features and to subsets of that set, not only can one detect and localize brain function but one can also characterize the unique elements of different functions.

Though the brain provides an exemplary of a complex system to which application of the SIGFRIED method is well-suited, there are numerous other types of complex systems amenable to this same method. Some of these examples include fluctuating financial markets (see, FIG. 6). By assessing multiple fluctuating measures of the financial market, the SIGFRIED method can ascertain subtle relationships and changes that would otherwise not be apparent. Other complex systems that can be analyzed to isolate substantive changes or prospectively detect changes from baseline activity also include other physiological, but non-brain signals (such as data recorded during sleep apnea studies (see, FIG. 5)), environmental weather indices, functioning of complex machinery, multi-step chemical and manufacturing processes, astronomical phenomena (e.g., solar flares), monitoring of complex communication systems (e.g., security monitoring for Internet chatter), and population monitoring for disease outbreaks.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate methods and systems consistent with the present invention. It should be appreciated by those of skill in the art that the techniques disclosed in the examples that follow represent approaches that the inventors have found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Signal Modeling for Real-Time Identification and Event Detection in Epilepsy Patients Electrocorticography (ECoG) activity was recorded in several patients with intractable epilepsy. ECoG is a technique of recording the electrical activity of the cerebral cortex by means of electrodes placed directly on it, either under the dura mater (subdural) or over the dura mater (epidural) but beneath the skull. Collection of ECoG signal activity can be conducted in accordance with the methods of US App. Pub. No. 2005-0131311, incorporated herein by reference. First, ECoG signals were recorded from 32 channels while the subject rested. Subsequently, signals were recorded from the same channels while the subject rested or moved her shoulder or hand in response to visual cues. Also, signals were recorded from the same channels while the patient protruded the tongue and said the word "move" in response to visual cues. In addition, signals were recorded from the same channels while the patient was shown flash cards that contained nouns and was asked to generate verbs corresponding to these nouns.

Data thus collected was processed by a methodology termed Signal Modeling for Real-Time Identification and Event Detection, or SIGFRIED. For each time point t in the resting data set, the vector of frequency domain amplitudes $X_t = [x_{1,t}, \ldots, x_{D,t}]$ was used as input to a modified version of the CEM algorithm (Celeux and Govaert, 1992). This procedure produced a model consisting of Y Gaussian distributions that approximate the statistical distribution of the features in the resting data set. Each of these Gaussian distributions j is characterized by a mean feature vector $\mu_j$, a covariance matrix $\Sigma_j$, and a prior probability $w_j$.

The fit of the Gaussian mixture model to the original distribution was assessed using the maximized negative log likelihood $L_j$ calculated for all Y Gaussian distributions j in the resting data distribution $$\left( L_j = \sum_{t=1}^{N_j} -\log\left(\frac{w_j}{(2\pi)^{\frac{D}{2}}|\Sigma_j|^{\frac{1}{2}}} e^{-\frac{m(X_t|j)}{2}}\right), \, m(X_t \mid j) = (X_t - \mu_j)^T \Sigma_j^{-1} (X_t - \mu_j) \right).$$

Furthermore, the number of distributions Y was automatically determined by iteratively choosing Y such that it minimized the Akaike Information Criterion $$\left( AIK(Y) = -2 \sum_{j=1}^{Y} L_j + 2N_p, \right.$$

where $N_p$ is the number of parameters in the model (Akaike, 1973)). The Akaike Information Criterion examines the complexity of the model together with goodness of its fit to the sample data, and produces a measure which balances between the two so as to find the minimal model that correctly explains the data.

When applied to a new data point, the output of the above process, termed Signal Modeling for Real-Time Identification and Event Detection (SIGFRIED), was the negative log likelihood L calculated for that single point.

Figure 1:
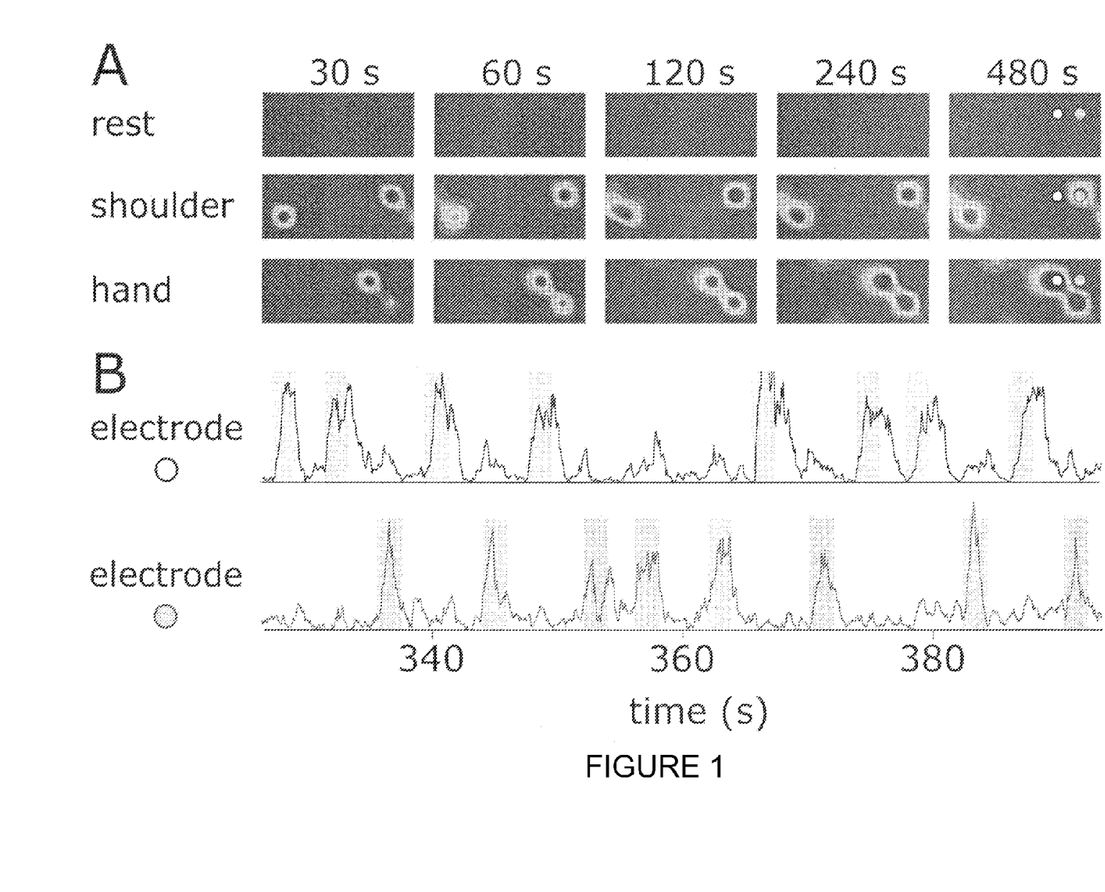
FIG. 1 is a series of ECoG images and traces depicting real-time visualization of brain function.
Figure 2:
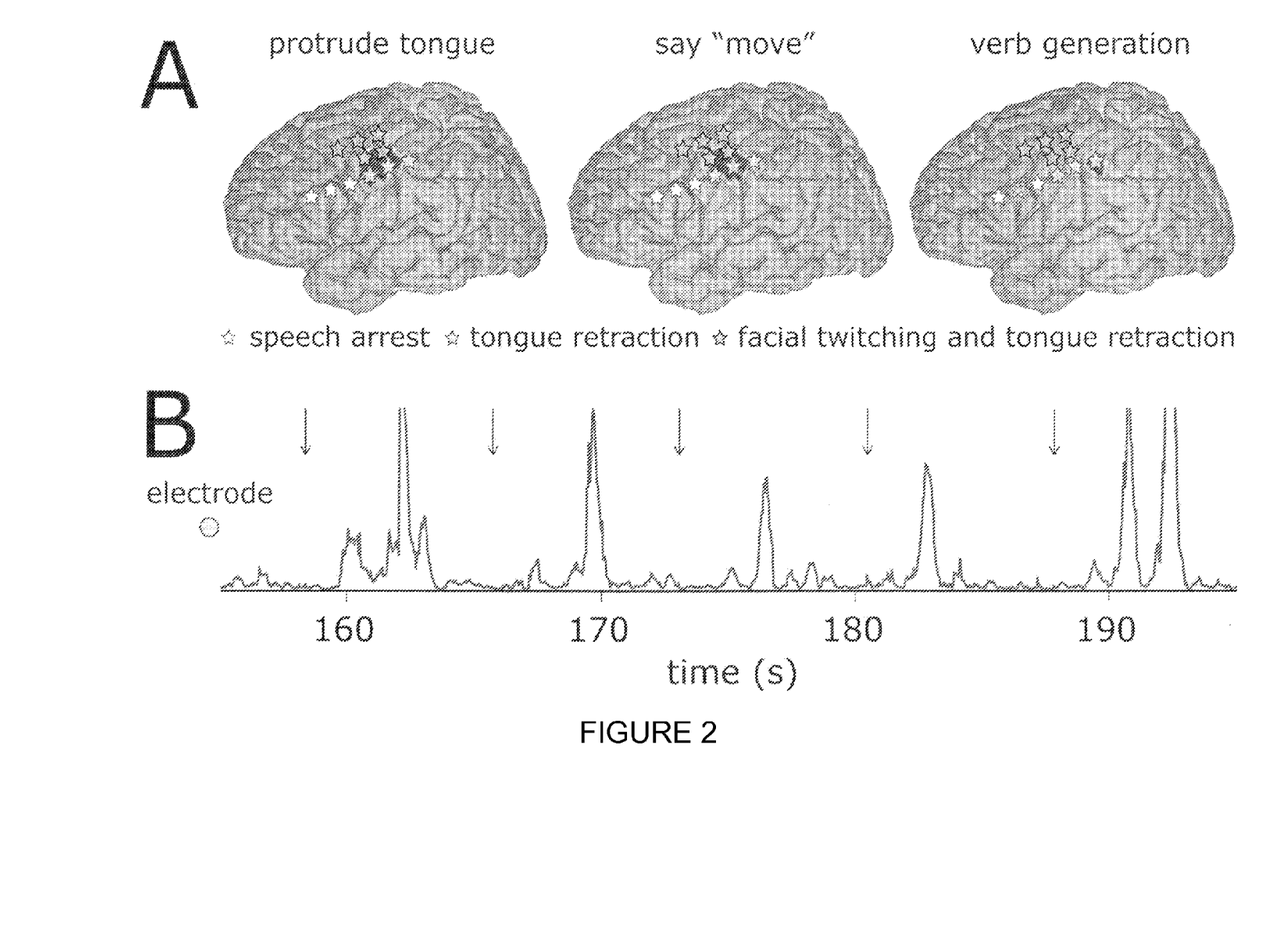
FIG. 2 is a series of brain images and traces depicting language and sensorimotor mapping without electrical stimulation and comparing it to mapping with conventional electrical stimulation.

Results showed that in multiple patients with subdural grid recordings, activity at distinct and reproducible grid locations corresponded to specific tasks, and interpretable results could be derived and visualized in real time (see, e.g., FIG. 1, FIG. 2).

FIG. 1 is a series of ECoG images and traces depicting real-time visualization of brain function. FIG. 1A is a series of images depicting the running averages of the output calculated using SIGFRIED as described herein, for the three conditions of rest, shoulder, and hand movement. Active locations for shoulder or hand are rapidly defined and remain stable over longer periods. From FIG. 1A, different locations that are active for shoulder or hand but not for rest are evident. From this figure, it is apparent that active locations are rapidly defined and remain stable over longer periods.

FIG. 1B is a pair of traces depicting (non-averaged) SIGFRIED time course responses for two electrodes responding to hand and shoulder movements. Shaded bars indicate times of cue presentation. FIG. 1B demonstrates that responses to hand or shoulder movement can also be readily identified without averaging, which would support rapid clinical testing.

FIG. 2 is a series of brain images and traces depicting language and sensorimotor mapping without electrical stimulation and comparing it to mapping with conventional electrical stimulation. FIG. 2A is a series of brain images that depicts activations calculated using SIGFRIED. Stars indicate locations identified using conventional electrical stimulation while darkened areas indicate activations calculated using SIGFRIED. FIG. 2A shows congruence between electrical stimulation locations and activations calculated using SIGFRIED. FIG. 2B is a trace depicting the SIGFRIED time course response for the electrode that was responsive to the verb generation task. Arrows indicate times of cue presentation.

Figure 3:
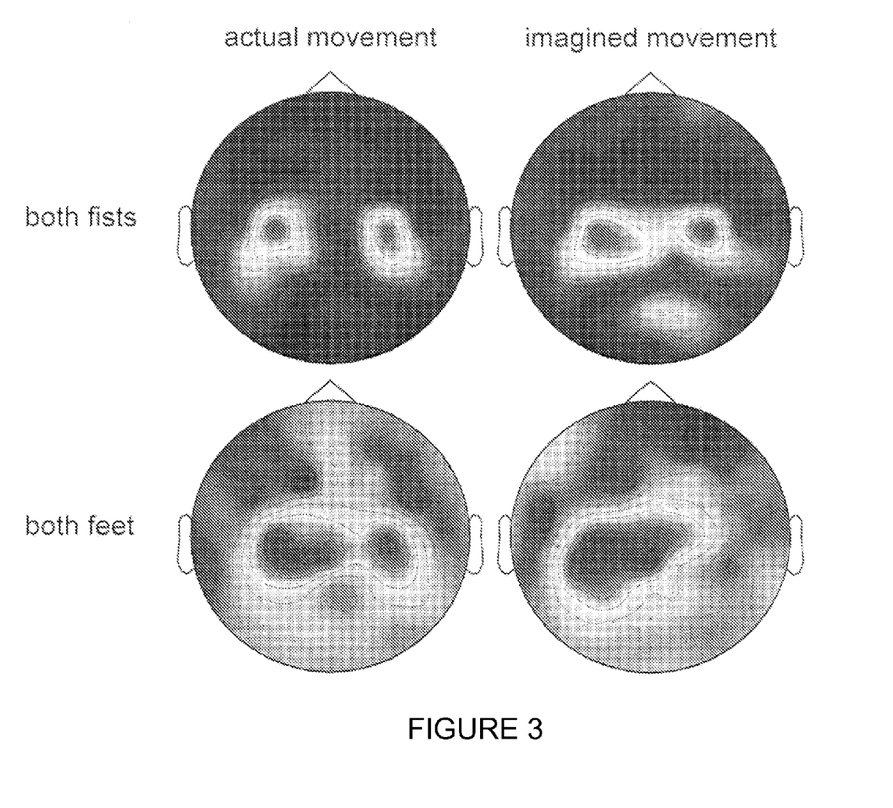
FIG. 3 is a series of images depicting identification and localization of activity associated with actual or imagined motor tasks.

FIG. 3 is a series of images depicting identification and localization of activity associated with actual or imagined motor tasks. Images are topographic depictions of running averages of the output calculated using SIGFRIED for EEG signals (all relevant EEG frequencies, 10-30 Hz in 2-Hz bins) recorded from 64 scalp locations while the subject moved his/her fists or feet in response to visual cues, or imagined the same actions.

This demonstrates that responses of the brain to various tasks can be analyzed in a prospective fashion (i.e., without knowing which features of the recorded brain signals will change or how they will change). Furthermore, these results indicate that the techniques described herein provide a new clinical tool reducing or eliminating the need for stimulation-based mapping methods.

Example 2

Signal Modeling for Real-Time Identification and Event Detection in Normal Patients Performing Tasks In several normal individuals, EEG activity was recorded from 64 scalp locations of subjects during rest. Patients were then asked to perform a number of motor and/or motor imagery tasks and EEG activity was again recorded.

Data thus collected was processed by a methodology termed Signal Modeling for Real-Time Identification and Event Detection (SIGFRIED), as described in Example 1. SIGFRIED was trained on a 1-min baseline period that was recorded prior to the movement/imagery tasks. Relevant EEG frequencies (i.e., 10-30 Hz in 2-Hz bins) were used in the calculations.

Results showed that EEG activity at distinct and reproducible locations on the scalp corresponded to specific actual or imagery tasks (see, e.g., FIG. 3). From FIG. 3, different locations that show changes with the different tasks are evident. For example, FIG. 3 depicts differences between actual movement and imagined movement, as well as differences between actual or imagined movement of fists versus feet. Further, the topographies of the results achieved using SIGFRIED are similar to these achieved previously using conventional retrospective methods. Because SIGFRIED used a broad range of relevant EEG frequencies (i.e., 10-30 Hz in 2-Hz bins), similar results can be expected in other subjects.

This demonstrates that responses of the brain to various tasks can be analyzed in a prospective fashion (i.e., without knowing ahead of time which of the features of the recorded brain signals will change or how they will change). Furthermore, brain signal changes associated with motor imagery identified with the method described above can be used to support brain-computer interface (BCI) communication and control.

Example 3

Seizure Prediction

Several subjects with intractable epilepsy were monitored using subdural electrodes over a broad range of frequencies (i.e., 5-90 Hz in 5-Hz bins). Data thus collected were processed by a methodology termed Signal Modeling for Real-Time Identification and Event Detection (SIGFRIED), as described in Example 1. SIGFRIED was previously trained on a different dataset using the same range of frequencies (i.e., 5-90 Hz in 5-Hz bins).

Figure 4:
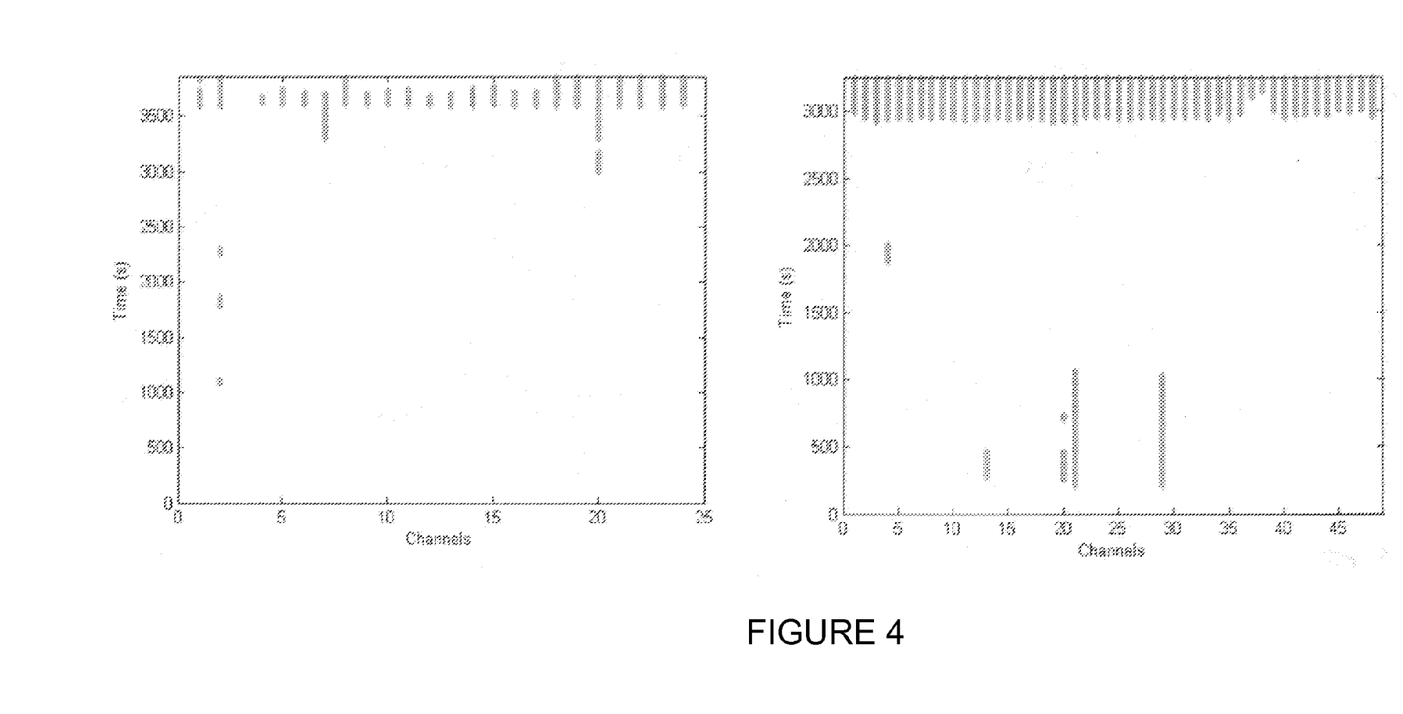
FIG. 4 is a pair of plots depicting the output calculated using methods and systems consistent with the present invention for subdural electrode signals over time as means of seizure prediction.

Results showed that seizures were readily detectable and, furthermore, predictable (see, e.g., FIG. 4). For example, from FIG. 4, seizures are detectable around times 3500 and 3000. In addition, several locations show abnormal activity prior to the seizure, thus providing the ability to predict the impending seizure. Because the detection threshold was the same and SIGFRIED was trained on a different dataset using the same broad range of frequencies (i.e., 5-90 Hz in 5-Hz bins), similar results can be expected in other subjects.

Example 4

Detection of Apnea Events in Sleep Studies

Figure 5:
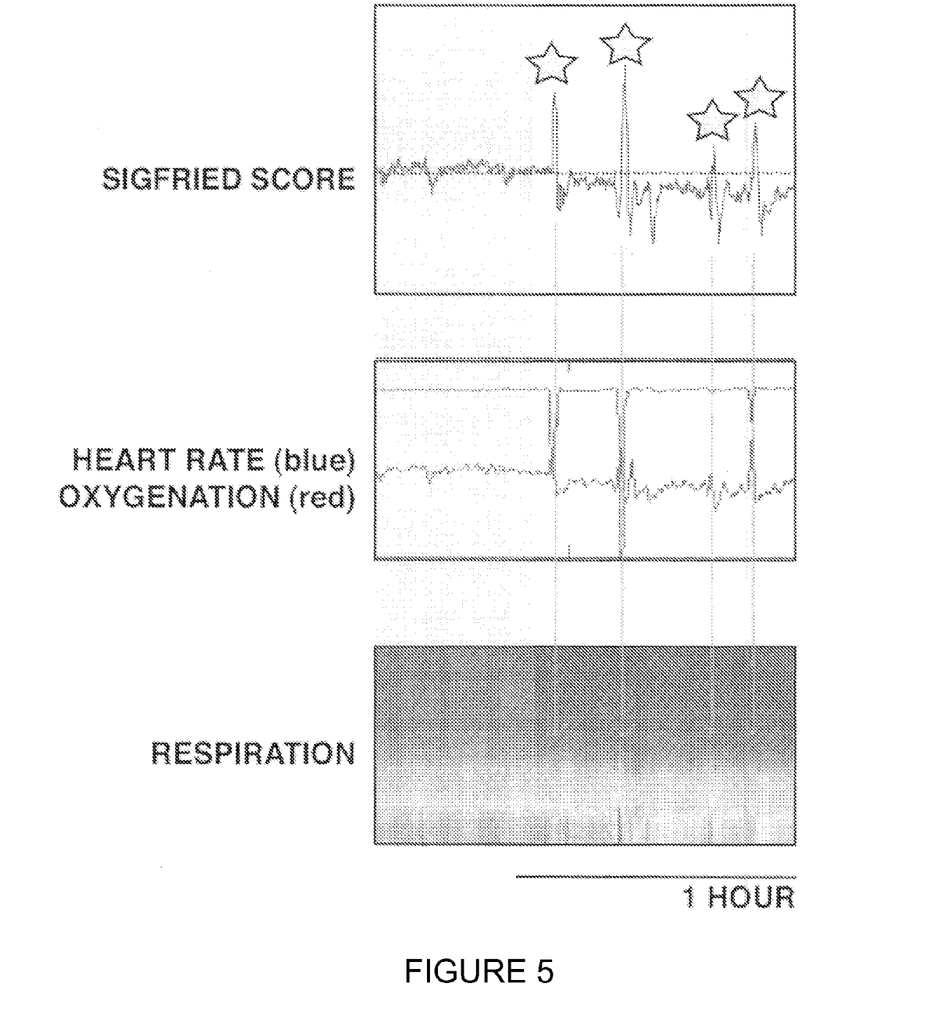
FIG. 5 illustrates application of methods and systems consistent with the present invention to data collected from a patient with sleep apnea.

SIGFRIED was applied to data collected during a sleep study of a patient with sleep apnea. FIG. 5 shows the results of inputting to SIGFRIED three different measurements: heart rate, oxygenation level, and respiration (bottom two panels). SIGFRIED used activity in these signals during the time indicated by the green shaded bar to establish reference activity. The top panel shows the output of SIGFRIED. At the times indicated by the stars, heart rate, oxygenation, and/or respiration show changes in activity, which is reflected in significant spikes produced by SIGFRIED. The results summarized in FIG. 5 demonstrate that SIGFRIED is applicable to analyzing complex signals of non-brain origin, and that is useful for such applications.

Example 5

Other Complex Systems: Detection of Commodity Index Fluctuations

Figure 6:
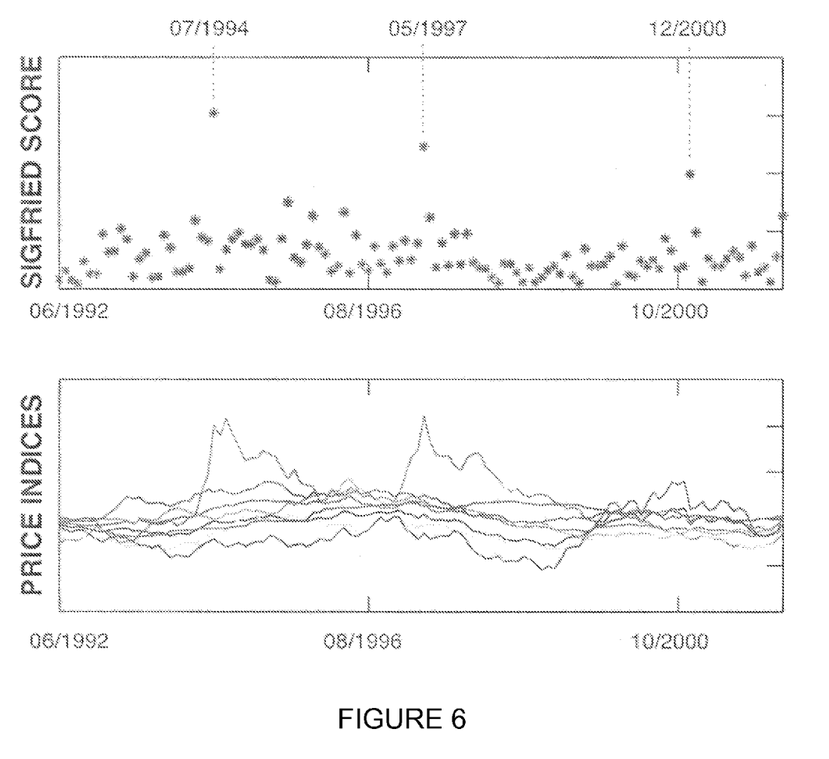
FIG. 6 demonstrates that methods and systems consistent with the present invention may be applied to signals from other complex systems.

FIG. 6 demonstrates that SIGFRIED may also be applied to signals from other complex systems of non-biological origin. The bottom panel of FIG. 6 shows price indices for eight different commodities from 1992 to 2002: all commodities index including petroleum; non-fuel commodities index; food index of cereals, oils, protein meals, meat, sugar, and bananas; index of beverages, coffee, cocoa, and tea; agricultural raw materials index; metals index; fertilizers index; and average petroleum spot index. Indices from a preceding baseline period (i.e., 01/1980-06/1992) were input to SIGFRIED to establish normal activity patterns. SIGFRIED prospectively analyzed activity patterns beyond this baseline period and detected three events (07/1994, 05/1997, and 12/2000) at which development of indices displays abnormal changes.

Figure 7:
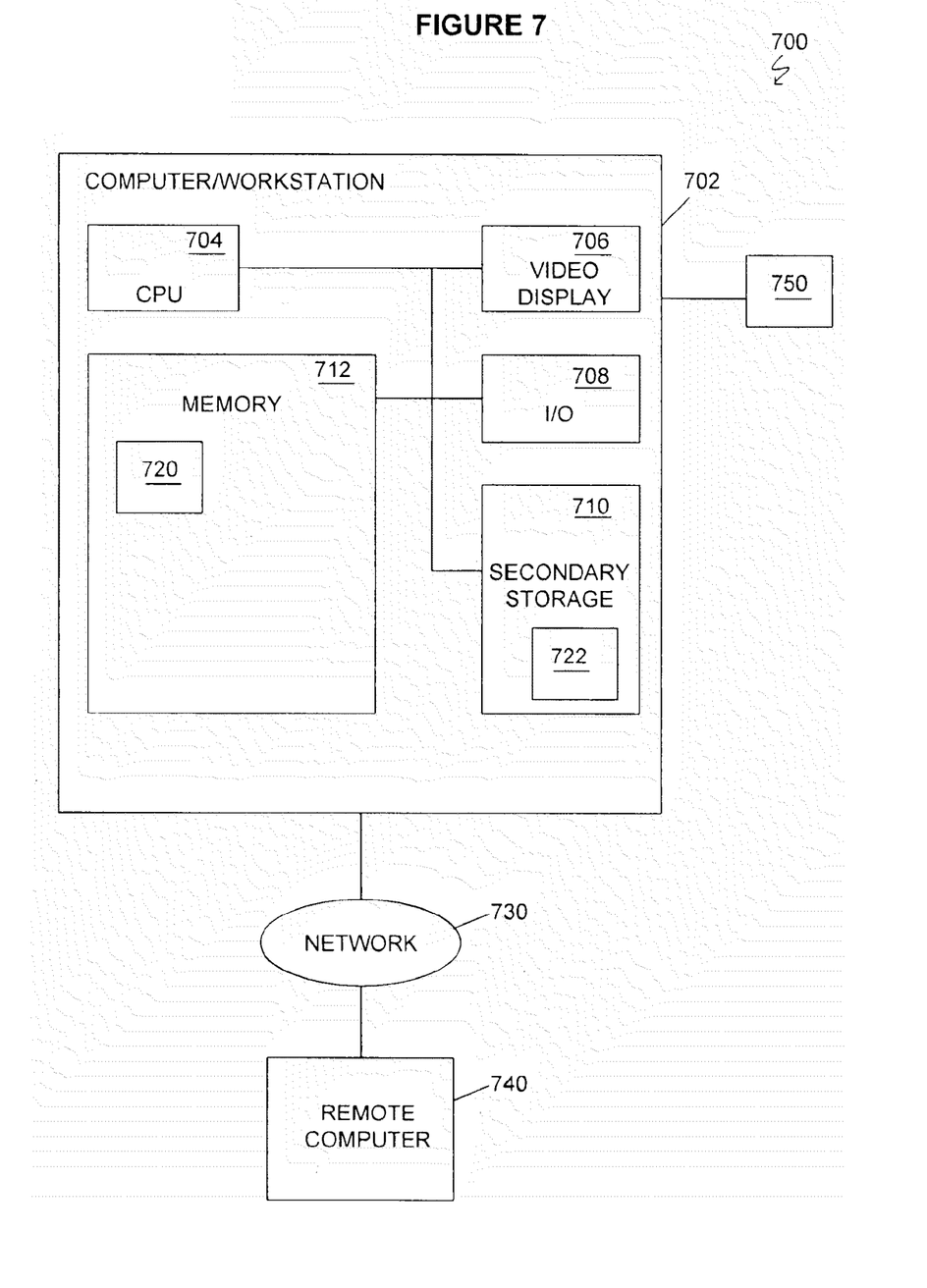
FIG. 7 depicts a block diagram of a data processing system suitable for use with the present invention.

FIG. 7 depicts a block diagram of a data processing system 700 suitable for use with methods and systems consistent with the present invention. Data processing system 700 comprises a plurality of computer or workstation 702 connected via a network 730 to a remote computer or workstation 740. The network is of a type that is suitable for connecting the computers for communication, such as a circuit-switched network or a packet-switched network. Also, the network may include a number of different networks, such as a local area network, a wide area network such as the Internet, telephone networks including telephone networks with dedicated communication links, connection-less networks, and wireless networks. In the illustrative example shown in FIG. 7, the network is a local area network. Each of the computers shown in FIG. 7 is connected to the network via a suitable communication link, such as a dedicated communication line or a wireless communication link.

In the illustrative example, workstation 702 that can receive complex signals from an external source 750, such as EM, EEG or ECoG signals. Workstation 702 comprises a central processing unit (CPU) 704, an input output (I/O) unit 708, a display device 706, a secondary storage device 710, and a memory 712. Workstation 702 may further comprise standard input devices such as a keyboard, a mouse, a digitizer, or a speech processing means (each not illustrated).

Workstation 702's memory 712 includes a program 720 for performing data acquisition and signal analysis as described above with respect to methods consistent with the present invention. The data may be acquired from the external source 750 or retrieved from secondary storage. Processing results may be stored locally, such as in file 722, or remotely, such as at remote computer 740.

Although aspects of methods, systems, and articles of manufacture consistent with the present invention are depicted as being stored in memory, one having skill in the art will appreciate that these aspects may be stored on or read from other computer-readable media, such as computer-readable storage media including secondary storage devices, like hard disks, floppy disks, CD-ROM, or other forms of ROM or RAM either currently known or later developed; or transmission media such as a carrier wave received from a network such as the Internet. Further, although specific components of data processing system 100 have been described, one having skill in the art will appreciate that a data processing system suitable for use with methods, systems, and articles of manufacture consistent with the present invention may contain additional or different components.

Figure 8:
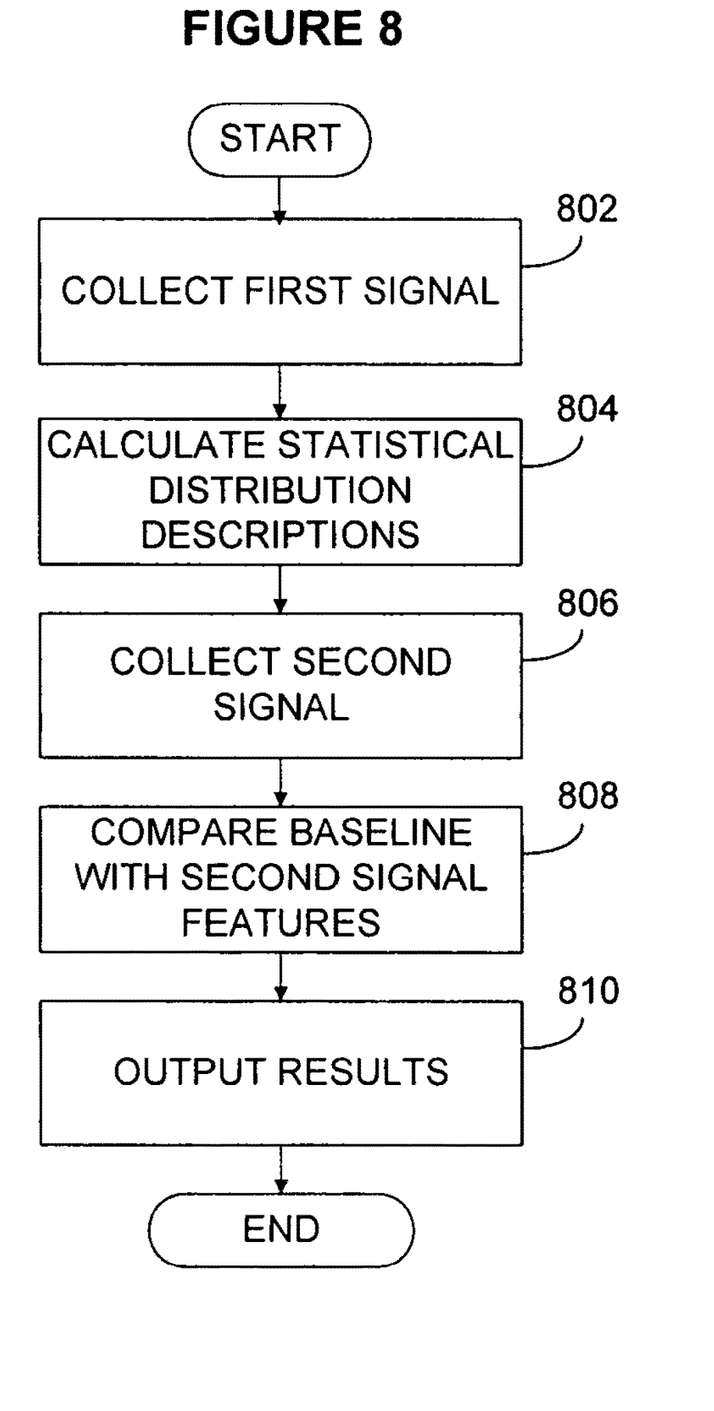
FIG. 8 is a flow diagram that depicts illustrative steps for analyzing signals consistent with the present invention.

FIG. 8 depicts a flow diagram illustrating exemplary steps performed by the program for analyzing complex consistent with the methods described above that are consistent with the present invention. First, the program collects a first signal, such as a first EM brain signal from a subject under a null condition (step 802). This can be done, for example, by reading the first signal from secondary storage or receiving the signal from external source 750. Then, the program calculates a statistical distribution description for each signal feature of the first signal to establish a signal features baseline (step 804). Calculating a statistical distribution description for each signal feature is described above.

After establishing the baseline, the program collects a second signal, such as a second brain signal from the subject during a non-null condition (step 806). The program then compares the signal features baseline with the signal features of the second signal to detect an event, such as a brain event (step 808). Calculating a statistical distribution description for each signal feature is described above. The results may be stored and outputted to the user, for example by displaying the results on the display device (step 810).

It is to be understood that methods and systems consistent with the present invention have been described in detail by way of illustration and example in order to acquaint others skilled in the art with the invention, their principles, and their practical application. Particular formulations and processes consistent with the present invention are not limited to the descriptions of the specific embodiments presented, but rather the descriptions and examples should be viewed in terms of the claims that follow and their equivalents. While some of the examples and descriptions above include some conclusions about the way the invention may function, the inventor does not intend to be bound by those conclusions and functions, but puts them forth only as possible explanations.

It is to be further understood that the specific embodiments consistent with the present invention as set forth are not intended as being exhaustive or limiting of the invention, and that many alternatives, modifications, and variations will be apparent to those skilled in the art in light of the foregoing examples and detailed description. Accordingly, methods and systems consistent with the present invention are intended to embrace all such alternatives, modifications, and variations that fall within the spirit and scope of the following claims.

What is claimed is:

1. A computer-implemented method executed in an electronic data processing system having a computer program stored on computer readable media, the computer program for analyzing complex signals, the computer-implemented method comprising:

obtaining, at the electronic data processing system, a first electronic signal representative of a first recorded brain signal of a living subject, the first electronic signal having a plurality of brain signal features, the first recorded brain signal having been recorded during a null condition when the living subject is not performing a task or receiving stimuli and is not in the midst of an epileptic event;

calculating, by the electronic data processing system and using the first electronic signal, a brain signal features baseline comprising a statistical distribution description for each brain signal feature, the brain signal features baseline modeling, for the null condition, a likelihood of fluctuation of each brain signal from a baseline value in the null condition;

obtaining, at the electronic data processing system, a second electronic signal representative of a second recorded brain signal of the living subject, the second electronic signal having a plurality of brain signal features, the second recorded brain signal having been recorded during a non-null condition of the living subject having been asked to perform a task or in the process of performing a task or the living subject receiving a form of stimuli; and comparing, by the electronic data processing system, the brain signal features of the second recorded brain signal with the brain signal features baseline to detect statistical deviations representative of an event comprising an occurrence of functional activity of the living subject, the functional activity associated with the performance of the task or the reception of stimuli.

2. A method according to claim 1 that occurs in real-time.

3. A method according to claim 1 wherein the first and second electronic signals comprise electromagnetic (EM) signals from a physiological system.

4. A method according to claim 3 wherein the first and second electronic signals comprise electromagnetic (EM) signals of brain activity in the living subject.

5. A method according to claim 4 wherein the electromagnetic (EM) signals comprise electrocorticographic (ECoG) signals.

6. A method according to claim 4 wherein the non-null condition comprises the subject performing a task.

7. A method according to claim 6 wherein the task is selected from the group consisting of a motor task and a language task.

8. A method according to claim 4 wherein the non-null condition comprises the subject receiving a stimulus.

9. A method according to claim 4 wherein the event comprises an event of abnormal brain activity.

10. A method according to claim 9 wherein the abnormal brain activity comprises seizure activity.

11. A method according to claim 9 wherein the abnormal brain activity comprises brain activity associated with a condition selected from the group consisting of stroke, demyelinating diseases, brain trauma, tumor, metabolic injury, epilepsy, meningitis, encephalitis, lead exposure, and developmental brain abnormalities.

12. A method according to claim 4 wherein the event comprises normal brain activity.

13. A method according to claim 12 wherein the normal brain activity comprises changes in brain activity associated with the non-null condition of the subject.

14. A brain computer interface system comprising:
a plurality of brain electrodes for obtaining electromagnetic (EM) signals from the brain of a living subject;
an electronic data processing system configured to gather, store and process EM signals obtained from the plurality of brain electrodes, the electronic data processing system comprising an executable computer program that when executed by a processing unit performs the following functions:
collect a first EM brain signal from the living subject under a null condition when the living subject is not performing a task or receiving stimuli and is not in the midst of an epileptic event;
calculate, using the first EM brain signal, a brain signal features baseline comprising a statistical distribution description for each brain signal feature of the first EM brain signal, the brain signal features baseline modeling, for the null condition, a likelihood of fluctuation of each brain signal from a baseline value in the null condition;
collect a second EM brain signal from the living subject during a non-null condition of the living subject having been asked to perform a task or in the process of performing a task or the living subject receiving a form of stimuli;
compare brain signal features of the second EM brain signal with the brain signal features baseline to detect statistical deviations representative of an event comprising an occurrence of functional activity associated with the performance of the task or the reception of stimuli.

15. A system according to claim 14 wherein the plurality of brain electrodes comprises electroencephalographic (EEG) recording electrodes.

16. A system according to claim 14 wherein the plurality of brain electrodes comprises electrocorticographic (ECoG) recording electrodes.

* * * * *